United States Patent [19]

Kolts

[11] Patent Number: 4,471,151

[45] Date of Patent: Sep. 11, 1984

[54] HYDROCARBON CRACKING PROCESS

[75] Inventor: John H. Kolts, Bartlesville, Okla.

[73] Assignee: Phillips Petroleum Company, Bartlesville, Okla.

[21] Appl. No.: 456,156

[22] Filed: Jan. 6, 1983

[51] Int. Cl.$^3$ ............................................... C07C 4/02
[52] U.S. Cl. ................................. 585/651; 585/653; 585/648; 208/118
[58] Field of Search ...................... 585/648, 651, 653; 208/118

[56] References Cited

U.S. PATENT DOCUMENTS

| | | | |
|---|---|---|---|
| 2,168,840 | 8/1939 | Groll. | |
| 2,319,710 | 5/1943 | Stratford et al. | 208/118 |
| 2,415,477 | 2/1947 | Folkins | 585/651 |
| 2,723,300 | 11/1955 | Lewis, Jr. | 585/648 |
| 3,580,961 | 5/1971 | Gath et al. | 585/648 |
| 3,773,850 | 11/1973 | Tischler et al. | |
| 3,803,260 | 4/1974 | Porchey et al. | 585/653 |

FOREIGN PATENT DOCUMENTS

| | | | |
|---|---|---|---|
| 1468691 | 1/1963 | Fed. Rep. of Germany | 585/648 |
| 363051 | 12/1931 | United Kingdom | 208/118 |
| 822991 | 11/1959 | United Kingdom | 585/648 |
| 945448 | 1/1964 | United Kingdom | 585/648 |
| 1141909 | 2/1969 | United Kingdom | 585/648 |
| 739081 | 6/1980 | U.S.S.R. | 585/648 |

*Primary Examiner*—Delbert E. Gantz
*Assistant Examiner*—Cynthia A. Prezluck
*Attorney, Agent, or Firm*—Edward L. Bowman

[57] ABSTRACT

A process for cracking a feed comprising at least one alkane involving contacting said feed with $H_2S$ and a high surface area contact material under cracking conditions.

24 Claims, 1 Drawing Figure

HYDROCARBON CRACKING PROCESS

BACKGROUND OF THE INVENTION

The present invention relates to the cracking of light hydrocarbons. In another aspect, the present invention relates to a method of increasing the conversion and in some cases the selectivity obtained during the cracking of light hydrocarbons.

It is well known that the product distributions obtained in the cracking of hydrocarbons are non-selective and, even at low conversions, produce a large number of primary products. Obviously, it would be preferable to obtain more selectivity to the specific desired products since such would give greater yields of the desired product and would in many cases make separation of the desired product less expensive.

In addition to poor selectivity, thermal cracking reactions are also known to require large inputs of energy to achieve high conversion levels. Accordingly, there is a need to increase the conversion level of such processes so that one can either use less energy or make more of the desired product in order to counterbalance the energy costs.

It has been known for several years that $H_2S$ can change the conversion level of hydrocarbon pyrolysis reactions and alter the selectivity to various products. Theories for explaining the effect of the $H_2S$ are presented in Scacchi et al, *Int. J. Chem. Kinetics,* 2, 115 (1970); Saige et al, *C. R. Acad. Sc. Paris,* 274, 322 (1972); Rebick, *Frontiers of Free Radical Chemistry,* Academic Press, Inc. (1980); and Rebick, *Ind. Eng. Chem. Fundam,* 20, 54 (1981). The present invention is based upon the discovery that the cracking of light hydrocarbons in the presence of $H_2S$ and certain high surface area materials increases the conversion far beyond what one would expect from the effects of the $H_2S$ or the high surface area material alone.

SUMMARY OF THE INVENTION

In accordance with the present invention, a hydrocarbon feed comprising at least one alkane having 2 to 20 carbon atoms per molecule is contacted under cracking conditions with $H_2S$ and a solid contact material comprising silica having a surface are of at least 50 $m^2$/gram.

DETAILED DESCRIPTION OF THE INVENTION

Figure 1:
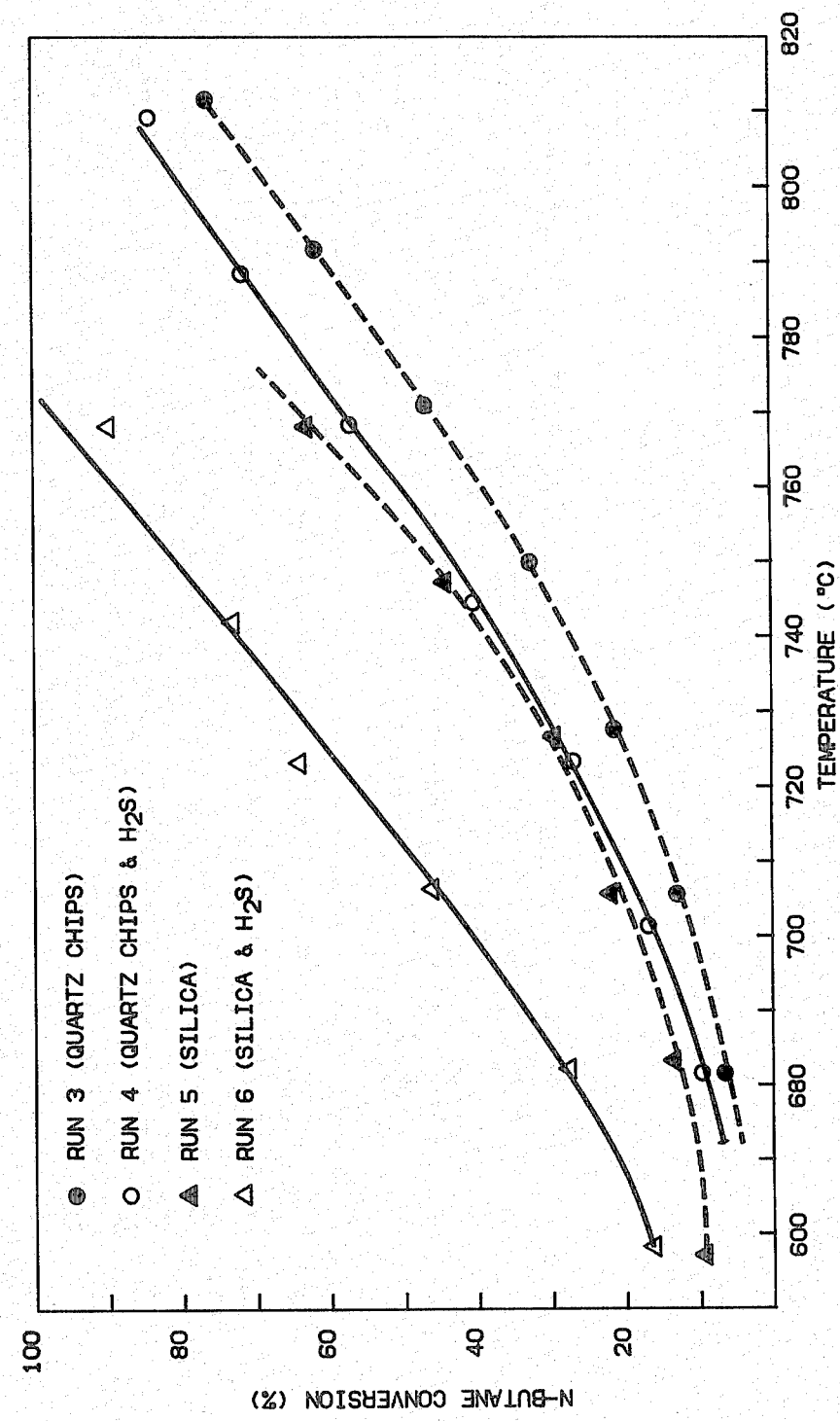
FIG. 1 is a graphical comparison of the relative effects of $H_2S$ on cracking carried out in the presence of low and high surface area materials.

The present invention is expected to provide at least some improvement in the cracking of any alkanes. However, since the cracking of higher molecular weight materials generally requires the employment of temperatures below those which give substantial decomposition of the $H_2S$, the invention is most useful in the cracking of alkanes having no more than 20 carbon atoms per molecule. The invention is especially useful in cracking alkanes containing 2 to 12 carbon atoms per molecule. Preferably, the feed consists essentially of hydrocarbons. Since the present invention has not been found to increase the cracking of olefins, the preferred feeds are those in which alkanes are the major hydrocarbon. More preferably, the feed consists essentially of hydrocarbons and contains at least 80 volume percent alkanes. The increased cracking is more notable for those alkanes having at least 4 carbons per molecule.

Any suitable cracking conditions can be employed and they will of course vary somewhat depending upon the nature of the hydrocarbon-containing feed. Typically though, the cracking will be conducted at a temperature in the range of about 400° C. to about 900° C., more preferably about 500° to about 800° C.

The currently preferred high surface area contact materials are silica gel. The contact material can have associated therewith other catalytically active material. Obviously, however, if the $H_2S$ adversely affects the activity of the catalytically active contact material then one does not obtain the advantages of this invention. The form in which the contact material is employed does not appear to significantly affect the observed benefits. In lab scale work, it has been common to use 20-40 mesh particles. In commercial scale work even ⅛ inch pellets have proven useful.

The amount of $H_2S$ employed can vary over a wide range. Typically the $H_2S$ will be employed in an amount in the range of 0.1 to 10 mole percent, more preferably 1 to 3 mole percent, based on the moles of alkane in the hydrocarbon feed. Most preferably the $H_2S$ is employed in an amount greater than that needed for substantially inhibiting carbon formation resulting from the presence of materials that tend to encourage carbon formation. The determination of the amount of $H_2S$ needed to substantially inhibit carbon formation can be readily determined for any selected cracking conditions by evaluating several $H_2S$ levels and noting the level at which there is no additional significant decrease in carbon formation. Typically after $H_2S$ has been passed through the reaction zone for some period of time there will be no additional significant decrease in the level of carbon formation. Thus, no matter what level of $H_2S$ is selected after enough has passed through the reaction zone one is carrying out the reaction in the absence of materials that are in a form that would cause any significant amount of carbon formation if the $H_2S$ were not employed. Once that point is reached then any level of $H_2S$ is obviously greater than that needed to substantially inactivate carbon formation.

It is theorized that the surprising improvement in cracking obtained over high surface area contact material is due to the fact that the higher surface area material acts as a catalyst for the decomposition of the $H_2S$. Accordingly, the contact time for the reaction can affect the results observed. Typically, the hydrocarbon feed is passed in contact with the contact material at a rate of about 100 to 4000 volumes of gaseous hydrocarbon feed per volume of contact material per hour, or more preferably 500 to 2500.

In some cases, particularly in small scale reactions, it is desirable to employ an inert diluent in conjunction with the hydrocarbon feed and the $H_2S$. The typical preferred diluent is nitrogen. Generally when the diluent is employed, it is employed in an amount no greater than about 3 times the combined volumes of the hydrocarbon feed and the $H_2S$.

The present invention and its benefits will be further illustrated by the following examples.

EXAMPLE I

This example illustrates the experimental setup for investigating the thermal cracking (pyrolysis) of alkanes. The reactor was a quartz tube having an outer diameter of about 8 mm and a length of 25 cm. It was filled with a single fixed bed of refractory oxide contact material about 6-10 cm high. The reactor was heated with a thermostatically controlled external heater. The reactor temperature was measured in the center of the catalyst bed by means of a thermocouple enclosed in an axial thermocouple well extending into the refractory oxide bed. Three feed streams were introduced into the reactor: various alkanes (either Phillips Petroleum Company pure grade or Matheson Gas Products research grade), a mixture of 10-20 mole percent of $H_2S$ (Matheson CP grade) and 80-90 mole percent of $N_2$, and air during the regeneration of the beds. These feed streams were introduced through the separate stainless steel feedlines each equipped with a flow meter, a flow control valve and an overpressure shutoff valve. The feedlines joined in a mixing T equipped with a pressure gauge and an overpressure control interfaced with the above-mentioned shutoff valves. The mixed feed streams, under a pressure of about 1 atm entered the reactor from the top.

The reactor effluent stream passed through an ice cooled trap, where liquid components were condensed. The gaseous components were usually snap sampled every two minutes and were analyzed for hydrocarbons (not for hydrogen) with a Perkin Elmer Sigma 3 chromatograph. Liquid samples were analyzed at the end of each run with a Hewlett Packard 5880 chromatograph containing a 50 ft OV-101 glass capillary column.

Data from the chromatograph were evaluated and expressed in terms of %-conversion (moles of converted feed hydrocarbon in effluent ÷ moles of feed introduced × 100), %-yield (moles of a specific product ÷ moles of feed introduced × 100), and %-selectivity (yield ÷ conversion × 100).

EXAMPLE II

Results of 14 representative pyrolysis runs employing n-butane plus, when desired, a mixture of $H_2S$ and $N_2$ and various refractory oxides of varying surface area are summarized in Table I. In runs employing $H_2S$ its concentration was 1 mole-% of the alkane feed.

TABLE I

| Refractory | Without $H_2S$ | | | With $H_2S$ | | | Difference in Conversion (%) | Relative Increase in Conversion (%) |
|---|---|---|---|---|---|---|---|---|
| | Run | Temp. (°C.) | Conversion (%) | Run | Temp. (°C.) | Conversion (%) | | |
| None | 1 (Control) | 641 | 3.2 | 2 (Control) | 635 | 4.9 | 1.7 | 53 |
| | | 666 | 6.3 | | 658 | 8.8 | 2.5 | 40 |
| | | 688 | 11.0 | | 680 | 14.6 | 3.6 | 33 |
| | | 713 | 25.5 | | 704 | 21.6 | — | — |
| | | 742 | 36.4 | | 747 | 44.7 | 8.3 | 23 |
| | | 763 | 48.2 | | 766 | 57.3 | 9.1 | 19 |
| | | 781 | 59.9 | | 785 | 69.6 | 9.7 | 16 |
| | | 800 | 72.0 | | 806 | 81.7 | 9.7 | 13 |
| | | 819 | 83.3 | | 824 | 91.5 | 8.2 | 10 |
| Quartz Chips | 3 (Control) | 682 | 6.8 | 4 (Control) | 682 | 9.6 | 2.8 | 41 |
| | | 706 | 12.8 | | 702 | 17.0 | 4.2 | 33 |
| | | 728 | 21.2 | | 723 | 26.7 | 5.5 | 26 |
| | | 750 | 32.9 | | 745 | 40.3 | 7.4 | 22 |
| | | 771 | 47.2 | | 768 | 56.6 | 9.4 | 20 |
| | | 792 | 62.2 | | 789 | 71.6 | 9.4 | 15 |
| | | 812 | 76.4 | | 809 | 83.7 | 7.3 | 10 |
| Silica (Surface Area = 317 $m^2/g$) | 5 (Control) | 657 | 10.1 | 6 (Invention) | 658 | 16.8 | 6.8 | 67 |
| | | 684 | 13.0 | | 682 | 28.6 | 15.6 | 120 |
| | | 706 | 21.7 | | 706 | 46.2 | 24.5 | 113 |
| | | 727 | 29.9 | | 724 | 64.5 | 34.6 | 116 |
| | | 748 | 44.5 | | 742 | 74.0 | 29.5 | 66 |
| | | 768 | 62.3 | | 768 | 90.1 | 27.8 | 45 |
| Silica (Surface Area = 314 $m^2/g$) | 7 (Control) | 665 | 8.5 | 8 (Invention) | 662 | 22.9 | 14.4 | 170 |
| | | 730 | 31.7 | | 723 | 61.1 | 29.4 | 93 |
| | | 753 | 49.6 | | 748 | 79.8 | 30.2 | 61 |
| | | 773 | 63.0 | | 769 | 89.4 | 26.4 | 42 |
| | | 791 | 77.1 | | 786 | 94.0 | 16.9 | 22 |
| Silica (Surface Area = 185 $m^2/g$) | 9 (Control) | 663 | 2.9 | 10 (Invention) | 661 | 7.3 | 4.4 | 152 |
| | | 687 | 5.4 | | 684 | 20.1 | 14.7 | 272 |
| | | 710 | 11.3 | | 711 | 41.6 | 30.3 | 268 |
| | | 752 | 32.9 | | 747 | 76.6 | 43.7 | 133 |
| | | 773 | 49.7 | | 769 | 90.0 | 40.3 | 81 |
| | | 792 | 66.8 | | 791 | 96.7 | 29.9 | 45 |
| Silica (Surface Area = 84.7 $m^2/g$) | 11 (Control) | 665 | 9.1 | 12 (Invention) | 655 | 18.1 | 9.0 | 99 |
| | | 690 | 14.5 | | 686 | 25.5 | 11.0 | 76 |
| | | 717 | 25.1 | | 708 | 38.0 | 12.9 | 51 |
| | | 731 | 36.1 | | 729 | 50.4 | 14.3 | 40 |
| | | 751 | 42.8 | | 751 | 66.9 | 24.1 | 56 |
| | | 774 | 67.5 | | 766 | 82.8 | 15.3 | 23 |
| Silica (Surface Area = 56.8 $m^2/g$) | 13 (Control) | 661 | 10.1 | 14 (Invention) | 661 | 18.4 | 8.3 | 82 |
| | | 689 | 13.1 | | 684 | 27.3 | 14.2 | 108 |
| | | 710 | 20.5 | | 707 | 54.2 | 33.7 | 164 |
| | | 730 | 30.7 | | 734 | 64.5 | 33.8 | 110 |
| | | 751 | 42.9 | | 749 | 77.1 | 34.2 | 80 |
| | | 772 | 59.7 | | 768 | 74.7 | 15.0 | 25 |
| | | 792 | 73.8 | | 785 | 89.4 | 15.6 | 21 |

Data in Table I show that at comparable reactor temperatures (660°-800° C.) and flow rates (200 cc/min n-$C_4$ and 200 cc/min $N_2$) the presence of 1 mole-% of $H_2S$ in the feed always caused an increase in n-butane conversion. However, this increase in conversion, both in absolute and relative terms, was unexpectedly much larger (20–270%; see Runs 5–14) in runs employing amorphorus $SiO_2$ (surface area: 57–317 m²/g, determined by BET $N_2$ adsorption) than in runs employing low surface area quartz chips (16–40 mesh) or no catalyst packing at all (4–44% increase in conversion; seen Runs 1–4). This unexpected difference in the effect of $H_2S$ on n-butane conversion is graphically illustrated for four of the 14 runs in FIG. 1. It is believed that there is an interaction between $H_2S$ and high surface area amorphous $SiO_2$, which is absent in low surface area crystalline $SiO_2$ such as quartz, and that this interaction unexpectedly promotes the pyrolysis of n-butane.

EXAMPLE III

This example illustrates another unexpected effect of $H_2S$ plus amorphous, high surface silica on the pyrolysis of n-butane. Results of detailed analysis of reactor effluents produced on silica with an without $H_2S$, each at a temperature selected to yield 80% conversion, are summarized in Table II.

TABLE II

| Refractory<br>Amount of $H_2S$<br>Weight-%<br>Temperature<br>(°C.) | Run 15 (Control)<br>Silica<br>(SA: 185 m²/g)<br>0<br>80%<br>800° C. | | Run 16 (Invention)<br>Silica<br>(SA: 185 m²/g)<br>1 volume or mole %<br>80%<br>753° C. | |
|---|---|---|---|---|
| | Weight-% | Mole-% | Weight-% | Mole-% |
| n-Butane | 20.8 | 10.8 | 20.4 | 11.6 |
| Isobutane | 0.3 | 0.2 | 0.4 | 0.2 |
| Butenes | 6.9 | 2.2 | 6.0 | 3.6 |
| Butadiene | 1.5 | 0.9 | 1.3 | 0.8 |
| Propane | 1.8 | 0.3 | 1.3 | 1.0 |
| Propylene | 23.7 | 18.3 | 35.0 | 28.6 |
| Ethane | 4.2 | 4.4 | 8.1 | 9.0 |
| Ethylene | 29.0 | 32.3 | 12.1 | 14.5 |
| Methane | 14.7 | 30.5 | 14.7 | 30.6 |

Data in Table II show two effects:

(a) the dehydrogenation of n-butane to butenes and butadiene is only a minor side reaction, and about 90% by weight of the products contain less than 4 C-atoms and are therefore formed by thermal cracking;

(b) unexpectedly the amount of propylene was considerably higher and the amount of ethylene was considerably lower when n-butane was pyrolyzed in the presence of amorphous silica plus $H_2S$ rather than on silica alone.

EXAMPLE IV

This example illustrates that the unexpected effect of silica plus $H_2S$ on the conversion of n-butane described in Example II was also observed for other alkanes. Table III summarizes conversion data for ethane, propane, isobutane and n-decane on low surface, crystalline $SiO_2$ (quartz chips) with an without $H_2S$ and on high surface, amorphous silica with an without $H_2S$, each at the same temperature and feed flow rate conditions.

TABLE III

| Run | Feedstock | Temp °C. | Refractory | $H_2S$ Added (Vol-%) | Conversion (%) | Relative Change in Conversion (%) |
|---|---|---|---|---|---|---|
| 17 (Control) | Ethane | 800 | Quartz Chips | 0 | 36 | −11 |
| 18 (Control) | Ethane | 800 | Quartz Chips | 1 | 32 | |
| 19 (Control) | Ethane | 800 | Silica | 0 | 48 | +46 |
| 20 (Invention) | Ethane | 800 | Silica | 1 | 70 | |
| 21 (Control) | Propane | 775 | Quartz Chips | 0 | 40 | +13 |
| 22 (Control) | Propane | 775 | Quartz Chips | 1 | 45 | |
| 23 (Control) | Propane | 775 | Silica | 0 | 41 | +24 |
| 24 (Invention) | Propane | 775 | Silica | 1 | 57 | |
| 25 (Control) | Isobutane | 750 | Quartz Chips | 0 | 38 | +18 |
| 26 (Control) | Isobutane | 750 | Quartz Chips | 1 | 45 | |
| 27 (Control) | Isobutane | 750 | Silica | 0 | 37 | +65 |
| 28 (Invention) | Isobutane | 750 | Silica | 1 | 61 | |
| 29 (Control) | n-Decane | 670 | Quartz Chips | 0 | 16 | +50 |
| 30 (Control) | n-Decane | 670 | Quartz Chips | 1 | 24 | |
| 31 (Control) | n-Decane | 670 | Silica | 0 | 22 | +145 |
| 32 (Invention) | n-Decane | 670 | Silica | 1 | 54 | |

Unexpectedly, the change in alkane conversion caused by 1 volume % of $H_2S$ was consistently higher with high surface silica (surface area: 317 m²/g) than with quartz chips. Detailed analytical data for Runs 29, 30, 31 and 32 are summarized in Table IV.

TABLE IV

| | | Quartz Chips | | Silica | |
|---|---|---|---|---|---|
| Product Component | | 29[1] (Control) | 30[2] (Control) | 31[1] (Control) | 32[2] (Invention) |
| $C_{10+}$ | (g per 100 g feed) | 0.15 | 0.17 | 0.17 | — |
| $C_{10}$ | (g per 100 g feed) | 84.3 | 76.47 | 77.90 | 46.20 |
| $C_{8+9}$ | (g per 100 g feed) | 0.68 | 2.75 | 1.88 | 4.56 |
| $C_7$ | (g per 100 g feed) | 1.56 | 2.07 | 1.51 | 5.07 |
| $C_6$ | (g per 100 g feed) | 1.59 | 1.89 | 1.43 | 3.75 |
| $C_5$ | (g per 100 g feed) | 1.41 | 0.95 | 0.84 | 2.24 |
| $C_4$ | (g per 100 g feed) | 2.50 | 2.82 | 2.47 | 7.95 |
| Propylene | (g per 100 g feed) | 1.82 | 3.10 | 3.27 | 7.29 |
| Propane | (g per 100 g feed) | 0.10 | 0.23 | 0.13 | 2.31 |
| Ethylene | (g per 100 g feed) | 3.90 | 6.14 | 6.38 | 10.10 |

TABLE IV-continued

|  | | Quartz Chips | | Silica | |
| --- | --- | --- | --- | --- | --- |
| Product Component | | 29[1] (Control) | 30[2] (Control) | 31[1] (Control) | 32[2] (Invention) |
| Ethane | (g per 100 g feed) | 1.01 | 1.92 | 1.31 | 5.73 |
| Methane | (g per 100 g feed) | 0.97 | 1.60 | 1.53 | 3.06 |

[1] flow rate was 1.18 g/minute n-decane, 203 cc/minute nitrogen
[2] flow rate was 1.18 g/minute n-decane, 170 cc/minute nitrogen and 30 cc/minute 13% $H_2S$ in nitrogen.

Data in Table IV show that at 670±5° C. the $H_2S$ over the silica produced a greater increase in $C_4$ to $C_7$ hydrocarbon production than the $H_2S$ over the quartz chips.

EXAMPLE V

This example illustrates the pyrolysis of n-butane on silica (surface area: 185 $m^2/g$) containing 10% by weight of transition metals, with and without $H_2S$. In the runs using no $H_2S$, the transition metals were employed as oxides. In the runs using $H_2S$, the catalysts were pretreated so that they were in the sulfide form prior to use in the cracking. Conversions and selectivities are summarized in Table V.

TABLE V

| Run | Catalyst | $H_2S$ Added (Mole-%) | Conversion (%) | Propylene Selectivity (%) |
| --- | --- | --- | --- | --- |
| 33 | Mo on Silica | 0 | 48 | 37 |
| 34 | Mo on Silica | 1.0 | 59 | 41 |
| 35 | W on Silica | 0 | 75 | 29 |
| 36 | W on Silica | 1.0 | 67 | 39 |
| 37 | Fe on Silica | 0 | 35 | 7 |
| 38 | Fe on Silica | 1.0 | 97 | 38 |
| 39 | Cr on Silica | 0 | 60 | 27 |
| 40 | Cr on Silica | 1.0 | 80 | 38 |

Data in Table V show that the use of $H_2S$ and high surface area contact material can also give a surprising increase in cracking activity even when the contact material has a catalytic metal associated therewith. Although the W sulfide catalyst of Run 36 was not as active as the W oxide catalyst of Run 35, it did provide greater selectivity to propylene.

What is claimed is:

1. A process for cracking comprising contacting a hydrocarbon feed comprising at least one alkane having 2 to 20 carbon atoms per molecule under cracking conditions with $H_2S$ and a solid contact material comprising silica having a surface area of at least 50 $m^2/gram$, wherein more $H_2S$ is employed than is needed for inhibiting carbon formation under said cracking conditions.

2. A process for cracking comprising contacting a hydrocarbon feed comprising at least one alkane having 2 to 20 carbon atoms per molecule under cracking conditions with $H_2S$ and a solid contact material comprising silica having a surface area of at least 50 $m^2/gram$, wherein the amount of $H_2S$ is greater than that needed to substantially inactivate the carbon forming activity of any materials present which in the absence of the $H_2S$ would catalyze carbon formation under said cracking conditions.

3. A process according to claim 2 wherein said cracking is carried out at a temperature in the range of about 400° C. to about 900° C.

4. A process according to claim 3 wherein said cracking is conducted in the absence of materials that are in a form that would cause any significant amount of carbon formation if said $H_2S$ were not employed.

5. A process according to claim 4 wherein said refractory material comprises silica gel.

6. A process according to claim 5 wherein said silica gel has a surface area in the range of about 50 $m^2/gram$ to about 350 $m^2/gram$.

7. A process according to claim 6 wherein said refractory material consists essentially of silica gel.

8. A process according to claim 7 wherein said hydrocarbon feedstream consists essentially of n-butane.

9. A process according to claim 7 wherein said hydrocarbon feedstream consists essentially of n-decane.

10. A process for cracking comprising contacting a feed comprising at least one alkane having 2 to 20 carbon atoms per molecule under cracking conditions with $H_2S$ and particles of silica gel having a surface area in the range of at least 50 $m^2/gram$ wherein more $H_2S$ is employed than is needed for inhibiting carbon formation under said cracking conditions.

11. A process according to claim 10 wherein said feed consists essentially of one or more alkanes each having 2 to 12 carbon atoms per molecule.

12. A process according to claim 11 wherein the major portion of the alkane in said feed is n-butane.

13. A process according to claim 12 wherein propylene is separated from the effluent of the cracking reaction.

14. A process according to claim 11 wherein the major portion of the alkane in said feed is n-decane.

15. A process according to claim 11 wherein said alkanes of said feed are selected from the group consisting of ethane, propane, isobutane, and n-decane.

16. A process according to claim 11 wherein said silica gel has a surface area in the range of about 80 to about 350 $m^2/gram$.

17. A process according to claim 16 wherein the $H_2S$ is employed in an amount in the range of about 1 to about 3 mole percent based on the total moles of alkane in said feed.

18. A process for cracking comprising contacting a hydrocarbon feed comprising at least one alkane having 2 to 20 carbon atoms per molecule under cracking conditions with $H_2S$ in a reaction zone containing a solid contact material comprising silica having a surface area of at least 50 $m^2/gram$, wherein said contact material has been contacted in said reaction zone with enough $H_2S$ that additional $H_2S$ does not provide any additional significant decrease in the level of carbon formation under the cracking conditions.

19. A process according to claim 18 wherein said feed consists essentially of n-butane and the product comprises propylene.

20. A process according to claim 19 wherein the $H_2S$ is employed in an amount in the range of 0.1 to 10 mole % based on the moles of n-butane.

21. A process according to claim 20 carried out at a temperature in the range of 500° C. to 800° C.

22. A process according to claim 21 wherein said solid contact material consists essentially of silica.

23. A process according to claim 22 wherein said solid contact material consists essentially of silica having a surface area in the range of 80 to 350 $m^2/gram$.

24. A process according to claim 23 wherein propylene is separated from the effluent of the cracking reaction.

* * * * *